US005626762A

United States Patent [19]
Priegnitz et al.

[11] Patent Number: 5,626,762
[45] Date of Patent: *May 6, 1997

[54] SEPARATIONS BY SIMULATED MOVING BED CHROMATOGRAPHY OPERATING AT LOW K' VALUES USING WEAKLY INTERATING ADSORBENTS AS THE STATIONARY PHASE

[75] Inventors: James W. Priegnitz, Elgin; Beth McCulloch, Clarendon Hills, both of Ill.

[73] Assignee: UOP, Des Plaines, Ill.

[*] Notice: The term of this patent shall not extend beyond the expiration date of Pat. No. 5,518,625.

[21] Appl. No.: 573,977

[22] Filed: Dec. 18, 1995

Related U.S. Application Data

[63] Continuation-in-part of Ser. No. 387,984, Feb. 13, 1995, Pat. No. 5,518,625.

[51] Int. Cl.[6] ............................................. B01D 15/08
[52] U.S. Cl. ........................................ 210/659; 210/198.2
[58] Field of Search ............................. 210/635, 656, 210/659, 198.2; 435/280

[56] References Cited

U.S. PATENT DOCUMENTS

| 5,126,055 | 6/1992 | Yamashita | 210/659 |
|---|---|---|---|
| 5,407,580 | 4/1995 | Hester | 210/635 |
| 5,433,793 | 7/1995 | Herber | 127/46.1 |
| 5,434,298 | 7/1995 | Negawa | 210/659 |
| 5,434,299 | 7/1995 | Negawa | 560/248 |

*Primary Examiner*—Ernest G. Therkorn
*Attorney, Agent, or Firm*—Thomas K. McBride; Eugene I. Snyder

[57] ABSTRACT

Resolution of a mixture of organic materials by simulated moving bed chromatography using a weakly interacting adsorbent as a stationary phase can be routinely effected with a liquid mobile phase characterized by atypically low values of k' with recoveries of at least 95% and a purity of at least 95%. In particular, values in the range 0.1<k'<1.0 are recommended with a resulting savings in mobile phase consumption, inventory, and recovery.

3 Claims, 5 Drawing Sheets

SEPARATIONS BY SIMULATED MOVING BED CHROMATOGRAPHY OPERATING AT LOW K' VALUES USING WEAKLY INTERATING ADSORBENTS AS THE STATIONARY PHASE

CROSS REFERENCE TO RELATED APPLICATION

This application is a continuation-in-part of U.S. application Ser. No. 08/387,984, filed Feb. 13, 1995, now U.S. Pat. No. 5,518,625 all of which is incorporated by reference.

BACKGROUND OF THE INVENTION

This application deals with the use of chromatography in commercial scale preparative separations. More particularly, our invention deals with the branch of simulated moving bed chromatography as applied to separations where the stationary phase interacts only weakly with adsorbed materials. Our contribution to such separations which is the subject of this application arises from the recognition that operating at low values of k', the capacity factor, is quite beneficial in such separations even though classical liquid chromatography theory teaches operation at high values of k' as one prerequisite to successful separations. To better understand our invention in the context of theory and conventional practice it will be helpful to briefly review some of the relevant principles of liquid chromatography.

One fundamental property in liquid chromatography is k', the capacity factor, which is defined as $$k' = \frac{n_s}{n_m} \quad (1)$$

where $n_s$ is the total moles of material being separated in the stationary phase and $n_m$ is the number of moles in the mobile phase. Where there are several components present, the capacity factor for the ith component is $$k'(i) = \frac{n_s(i)}{n_m(i)}$$

The retention time, $t_r$, for component i, $t_r(i)$, is related to the time it takes for the mobile phase to travel the length of the column, $t_0$, by the distribution of component between the stationary and mobile phases according to the equation, $$t_r(i) = \frac{t_0}{\left[\frac{n_m(i)}{n_m(i)+n_s(i)}\right]} = t_0 \frac{[n_m(i)+n_s(i)]}{n_m(i)}$$

$$t_r(i) = t_0[1 + k'(i)]$$

Rearranging, $$k'(i) = \frac{t_r(i) - t_0(i)}{t_0(i)} \quad (2)$$

Thus, the capacity factor k' also is related to the relative retention time of the component in question.

For two components, the milo of their relative retention times, α, is $$\alpha_{ij} = \frac{t_r(i) - t_0}{t_r(j) - t_0} = \frac{k'(i)}{k'(j)}$$

where $a_{ij}$ is the selectivity factor between components i and j. Finally, the volume, $V_r$, of the mobile phase required to elute a component as measured to the apex of the peak is related to the flow rate, F, of the mobile phase and retention time of the component by, $$V_r(i) = t_r(i) F$$

from which it follows that $$V_r(i) = V_0[1 + k'(i)] \quad (4)$$

$$[V_r(i) - V_0]/V_0 = k' \quad (5)$$

$$\frac{V_r(i) - V_0}{V_r(j) - V_0} = \frac{t_r(i) - t_0}{t_r(j) - t_0} = \frac{k'(i)}{k'(j)} = \alpha_{ij} \quad (6)$$

Thus, classical liquid chromatography theory as supported by much experimental evidence leads to the conclusions that the retention volume of a particular component, relative to the retention volume of the pure mobile phase, depends only on the capacity factor for the component, although relative retention volumes and relative retention times for two components depend only on the ratio of the two capacity factors, and it is the ratio of the capacity factors which define selectivity.

One form of chromatography well adapted to continuous, commercial-size separation is simulated moving bed chromatography. In continuous moving bed chromatography the stationary phase moves relative to the feed and mobile phase inputs, and the extract and raffinate outputs. Because of the difficulty in implementing a moving stationary phase in chromatographic separations its simulation is favored in practice (hence the name simulated moving bed chromatography) where incremental positional changes of the input and output streams, relative to a static stationary phase, is effected at regular intervals. Although many of the relations developed above apply to simulated moving bed chromatography some additional nuances are applicable when the separations are effected by weakly interacting adsorbents.

One important observation from the foregoing review of some salient theoretical aspects of liquid chromatography is the effect of k' on the retention time and retention volume, $$k' = t_r - t_0 = V_r - V_0$$

Whereas one normally seeks to maximize the difference in retention time between a component and the mobile phase in order to increase the difference in retention time between two components, this requires a large k' which has the ancillary undesirable effect of increasing the retention volume of the mobile phase for the components. Thus, the accepted practice in analytical chromatography and in batch mode preparative chromatography of operating at a high k', usually in the range 1<k'<10, has as a necessary consequence the usage of a large volume of mobile phase.

We have found the conditions in simulated moving bed chromatography can be significantly modified from those required for analytical and batch mode preparative chromatography. In particular, when weakly interacting adsorbents are used as the stationary phase, separations using simulated moving bed chromatography can be performed effectively at low values of k', thereby minimizing the amount of mobile phase which is needed. Specifically, such separations may be performed efficiently where k' is less than 1, and especially in the range 0.1<k'<1. Since an appreciable cost of the separation process is associated with the mobile phase and its recovery from the raffinate and extract streams, our process affords substantial cost savings accruing from a lower mobile phase inventory, lower utility costs in recovering the mobile phase, and other ancillary costs.

It needs to be mentioned that even though certain types of separation currently effected by simulated moving bed (SMB) processes operate at the equivalent of a low k' it is not obvious to extend this knowledge to separations using weakly interacting adsorbents as the stationary phase because the mechanism of adsorption is fundamentally different. Thus, the adsorbents used in traditional separations such as that of the xylene isomers are zeolites such as X faujasites that have a high ion exchange capacity. With zeolites, the primary mechanism for adsorption is electrostatic attraction. The heat of adsorption, which is a direct measure of strength of the bonding between the adsorbate and the surface, is high (typically ca. 20 kcal per mole). Consequently, a "strong" desorbent is required in these systems. Frequently, the desorbent is similar in polarity to that of the feed component. For example, xylenes are desorbed with alkyl aromatics such as p-diethylbenzene or toluene and chlorinated aromatic feedstocks are typical desorbed with chlorinated aromatic solvents. The strong adsorbate/adsorbent interaction and the high binding energies require the use of a strong desorbent.

The stationary phases which are the subject of this invention are weakly interacting adsorbents such as refractory inorganic oxides and related materials as exemplified by silica, alumina, titania, magnesia, layered double hydroxide as illustrated by hydrotalcite and related material, all of which are solids characterized by surfaces with free hydroxyl groups. The mechanism of adsorption for the latter materials is very different from that of zeolites in that weak van der Waals forces predominate. Using silica as an example, the adsorbate partitions between the hydroxyl-rich surface and molecules of the mobile phase. The binding energies between the weekly interacting adsorbent and the adsorbate may be less than 1 kcal per mole and the mobile phases are typically weak. Consequently, manipulation of the mobile phase composition and the use of "strong mobile phases" is unexpected for the very weak intermolecular interactions encountered with weakly interacting adsorbents as the stationary phase. We also shall see that solubility plays a more significant role in our invention than in prior SMB separations.

SUMMARY OF THE INVENTION

The purpose of this invention is to effect separations, especially of organic material, by simulated moving bed chromatography using as a stationary phase a weakly interacting adsorbent and using a conventional liquid mobile phase operating under separation conditions characterized by a low capacity factor for at least one of the separated materials. In an embodiment $0.1<k'<1.0$. In a more specific embodiment $0.3<k'<1.0$.

DESCRIPTION OF THE INVENTION

Figure 1:
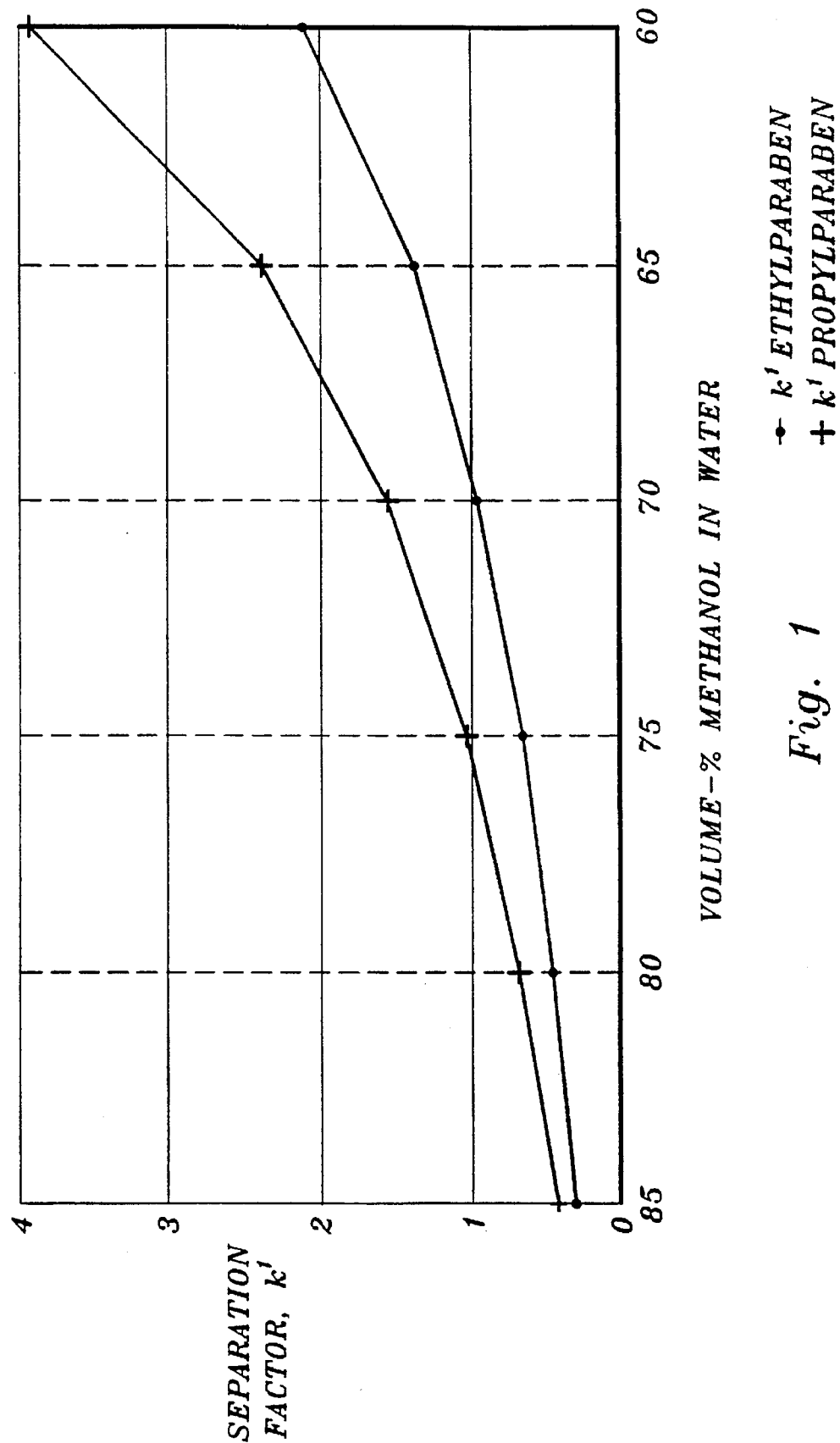
FIG. 1 depicts the effect of mobile phase composition on the separation factor.

Our invention results from the recognition that although a high value of retention capacity (i.e., capacity factor), k', is desirable and is usually posited as a necessary condition for the successful separation of two materials in traditional liquid chromatography, such a requirement is neither necessary nor desirable in effecting successful separations generally by simulated moving bed chromatography. Because the volume of the mobile phase used in eluting a material is proportional to k', a consequence of high k' values is a relatively large usage of the mobile phase. The larger the mobile phase usage, the higher the cost due to an increased solvent inventory, an increased cost of recovering the separated component from a larger volume of mobile phase, and higher inadvertent losses of mobile phase. Employing our invention leads to a substantial cost reduction and operating efficiency in effecting separations employing weakly interacting adsorbents as the stationary phase. In particular, our invention relates to the use of simulated moving bed chromatography for separations generally where one employs a conventional mobile phase and a solid stationary phase which interacts only weakly with the materials being adsorbed (adsorbates). The core of our invention is operating the SMB process under conditions where there is a low retention capacity for at least one of the materials separated, specifically $0.1<k'<1.0$ In traditional liquid chromatography $1.0<k'<10$. This condition has been used as both a desirable and necessary condition for adequate separation of components of interest. In simulated moving bed chromatography using a stationary phase which interacts only weakly with the adsorbates, we have found adequate separation can be achieved at $0.1<k'<1.0$. The benefits which flow need not be repeated; vide supra.

More particularly, the stationary phases to which our invention applies are adsorbents which interact only weakly with adsorbates. Such "weak interactions" are dominated by van der Waals forces with binding energies less than 4 kcal/mol, and usually in the range from 1 kcal/mol up to about 4 kcal/mol. In the context of our invention "weakly interactive adsorbents" are those whose binding energy to the adsorbate of interest is not more than about 4 kcal per mole. For example, the heat of adsorption of benzene on silica gel ranges from 1.2 to 3.8 kcal/mol, with the value depending upon the pretreatment temperature of the silica gel. Typical temperatures used in adsorption are 300° C. which corresponds to a heat of adsorption of 1.6 kcal.mol. See T. Morimoto and H. Naono, *Bull. Chem. Soc. Japan*, 45, p.700. Among the stationary phases of special interest in the context of our invention are the refractory inorganic oxides such as silica, alumina, titania, and magnesia, and the layered double hydroxide as illustrated by hydrotalcite. All of the foregoing are characterized by the presence of free surface hydroxyl groups, which are responsible for the weak adsorbent-adsorbate interactions of these materials.

Layered double hydroxides are a class of anionic clays. Among the anionic clays hydrotalcite is the best known and has the formula $Mg_6Al_2(OH)_{16}CO_3 \cdot 4H_2O$, with manasseite, a polymorph, having the same formula. Pyroaurite and sjogrenite are polymorphs of formula $Mg_6Fe_2(OH)_{16}CO_3 \cdot 4H_2O$. Among other naturally occurring clays having the formula $X_6^{2+}Y_2^{3+}(OH)_{16}CO_3 \cdot 4H_2O$ may be mentioned sfichfite and barbertonite, polymorphs with X=Mg and Y=Cr, takovite (X=Ni and Y=Al), reevesite (X=Ni and Y=Fe) and desautelsite (X=Mg and Y=Mn).

Although the foregoing formula is that of the "ideal" structure for hydrotalcite and its related minerals, it has been known for some time that analogous anionic materials more generally have the formula $[M(II)_{1-x}M(III)_x(OH)_2]^{x+}(A^{n-}_{x/n}) \cdot mH_2O$ (F. Cavani et al., *Catalysis Today*, 11, 173–301 (1991), at page 179) where x=0.25, n=2, m=4, and a=$CO_3$ corresponds to the foregoing cases. Using M(II)=Mg, M(III)

=Al, and $A=CO_3^=$ as an example, x may vary over a rather broad range of about 0.1 to 0.34, corresponding to a magnesium/aluminum ratio as high as 9 and as low as about 2. Such materials deviating from the formula for the "ideal" may be termed synthetic hydrotalcites and are included in the class of layered double hydroxides for the purpose of this invention.

In U.S. Pat. No. 3,879,523, 3,879,525, and 3,796,792 Miyata et al. describe "composite metal hydroxides having a layer [sic] crystal structure and to a process for the preparation of the same" of formula $$M_x^{2+}M_y^{3+}(OH)_{2x+3y-2z}(A^{2-})_z \cdot aH_2O$$

where the divalent metal could be copper, beryllium, calcium, strontium, barium, zinc, cadmium, tin, lead, manganese, magnesium, and metals of Group VIII, and the trivalent metal could be metals of Group III, titanium, metals of Group V, chromium, manganese, metals of Group VIII, the rare earths and actinides. These materials also are included within the class of layered double hydroxides for the purpose of our invention.

EXAMPLES

The methodology used to identify the conditions for simulated moving bed (SMB) operation is discussed and exemplified. The optimal conditions can be readily identified by analyzing elution profiles obtained from HPLC (high performance liquid chromatography). Important parameters for optimization are loadability of the support, selectivity, mobile phase strength, and feed solubility. Optimization of these parameters helps identify conditions suitable for a cost-effective separation.

The experimental approach is outlined below. Although we believe our general approach is effective and efficient, we do not mean to imply that other alternatives are unavailable. We make our choice based on convenience, efficacy, and experience.

1. Identify a suitable stationary phase.
2. Determine the solubility properties of the feed material.
3. Identify a mobile phase that gives the best combination of selectivity and solubility.
4. Evaluate the effect of different mobile phase compositions.
5. Select the optimal mobile phase composition subject to the parameters of feed solubility, selectivity, and mobile phase strength.

The following case study is presented to demonstrate how our experimental approach applied and illustrates the case where the selectivity is relatively insensitive to mobile phase and the solubility of the feed is high. In each example productivity and mobile phase consumption are calculated from elution profile data for various mobile phase compositions. Optimal SMB conditions are derived from the productivity and mobile phase consumption data.

DEFINITIONS

Productivity refers to the amount of product (in grams) processed per liter of stationary phase per hour.

Mobile phase consumption refers to the amount of solvent required to process one gram of feed.

Target performance in the SMB operation is 98% purity of the extracted component and 99% recovery, where recovery refers to the yield of the extracted component.

Separation of Diastereomeric Steroids. In this example of the separation of a steroid mixture the selectivity is not influenced by the mobile phase composition and the feed has good solubility.

Introduction. The separation of steroid diastereomers was performed on Kromasil silica with a mobile phase consisting of methylene chloride and methyl t-butyl ether (MTBE). The silica had a particle size of 16 µm and was packed in a column with 1.6 cm ID and 6 cm in length. The effect of the mobile phase composition on the performance of the SMB operation was evaluated.

Elution Profiles. A number of chromatograms were generated with a variety of methylene chloride/MTBE mobile phase compositions. Typical experimental conditions involved the use of a feedstock containing 1.0 wt % steroid mixture in methylene chloride. A 20 µL injection volume was used and the flow rate was 2.9 mL/min. The wavelength for detection was 240 nm and the sensitivity was 0.1 AUFS. The results are shown in Table 1.

SMB Performance. Target performance in the SMB operation was 98% purity of the alpha diastereomer, which is in the raffinate, and 99% recovery. The feed has good solubility in the mobile phase and 20 wt % feed concentration was assumed for all cases. A summary of the SMB performance is shown in Table 1.

Figure 2:
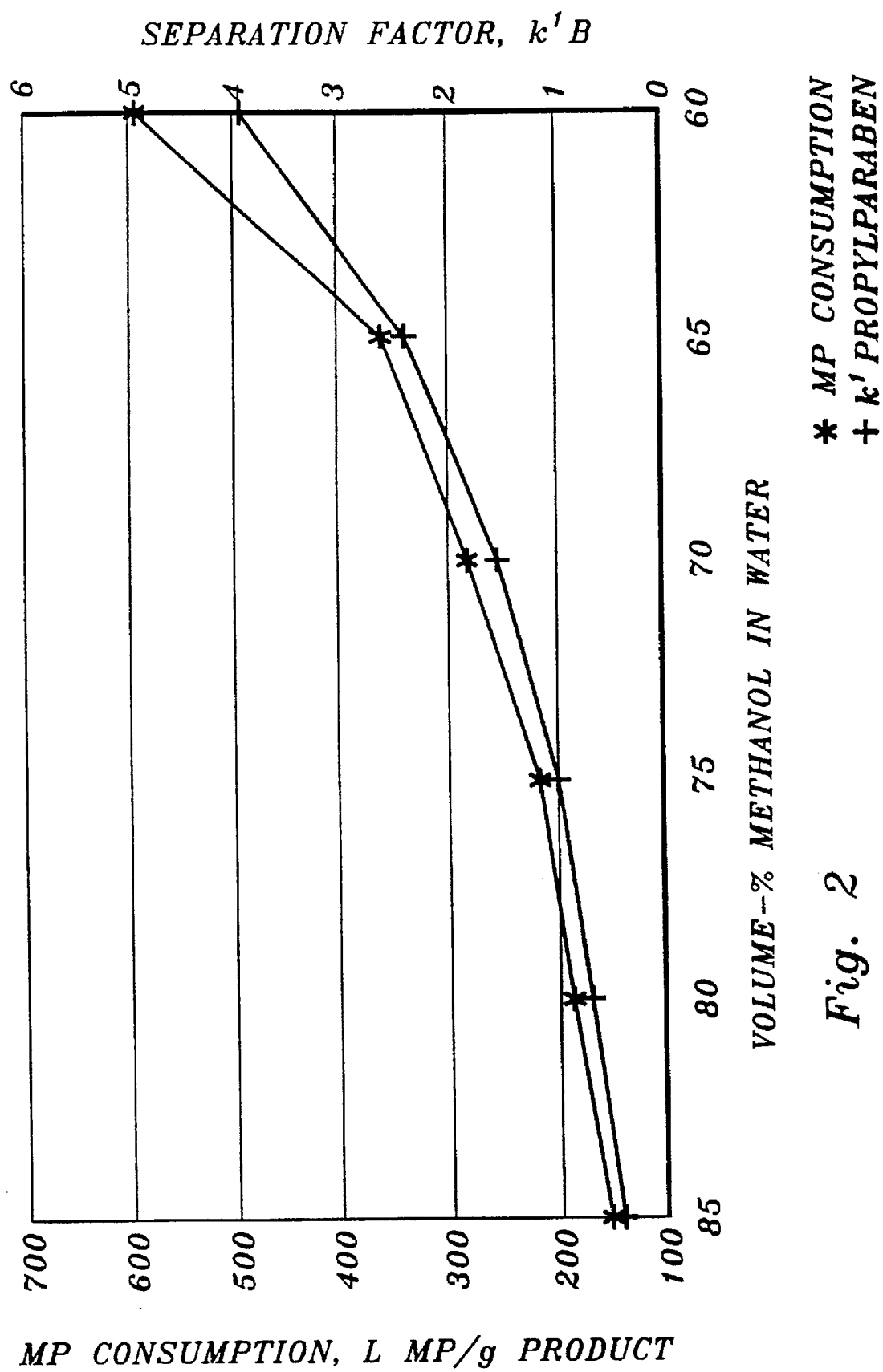
FIG. 2 depicts the change in mobile phase consumption versus the separation factor.

The elution profile data, shown in FIG. 1, indicates that the capacity factors, k', decrease as the amount of MTBE in the mobile phase increases. The mobile phase consumption in an SMB operation ranges from 172 liters of mobile phase per kilogram of product to 2,169 liters of mobile phase per kilogram of product. The increase in the mobile phase consumption correlates closely with the increase in the capacity factor, see FIG. 2. The preferred operating conditions, where mobile phase consumption is minimized, are with a mobile phase composition of 90/10 vol % methylene chloride/MTBE. At these conditions, the capacity factors are 1 or below.

Figure 3:
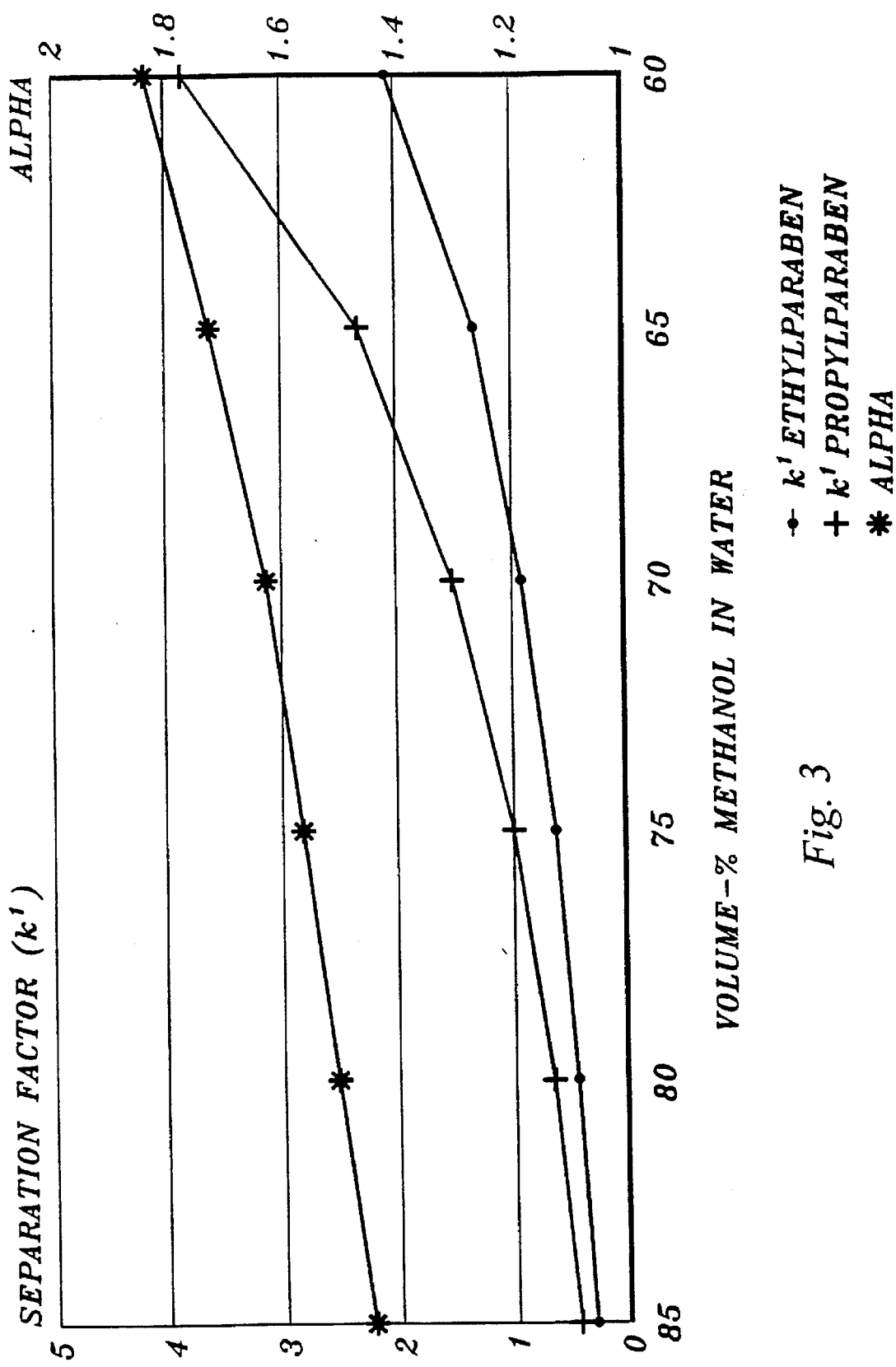
FIG. 3 depicts the change in selectivity versus separation.
Figure 4:
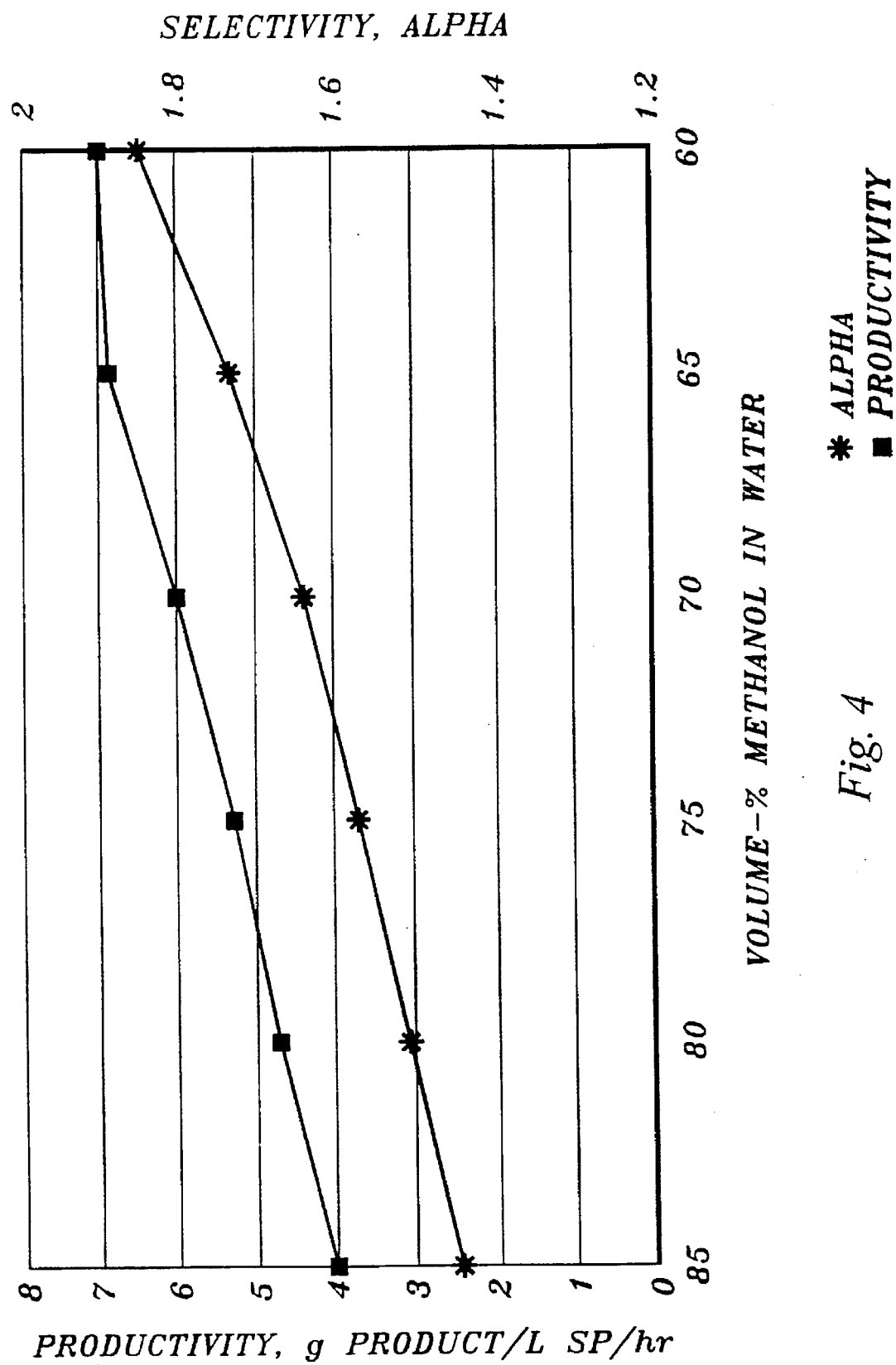
FIG. 4 depicts productivity versus selectivity.

The selectivity is not influenced by the mobile phase composition. The fluctuations in selectivity, shown in FIG. 3, are within experimental error. The productivity, defined as grams product per liter stationary phase per hour, ranges from 10 to 15.3. The increase in productivity as the amount of MTBE in the mobile phase decreases is attributed to a weaker mobile phase which competes less effectively with the feed. The increase in productivity with 90/10 vol % methylene chloride/MTBE mobile phase is due to the apparent increase in selectivity. The correlation between the productivity and selectivity is shown in FIG. 4.

Figure 5:
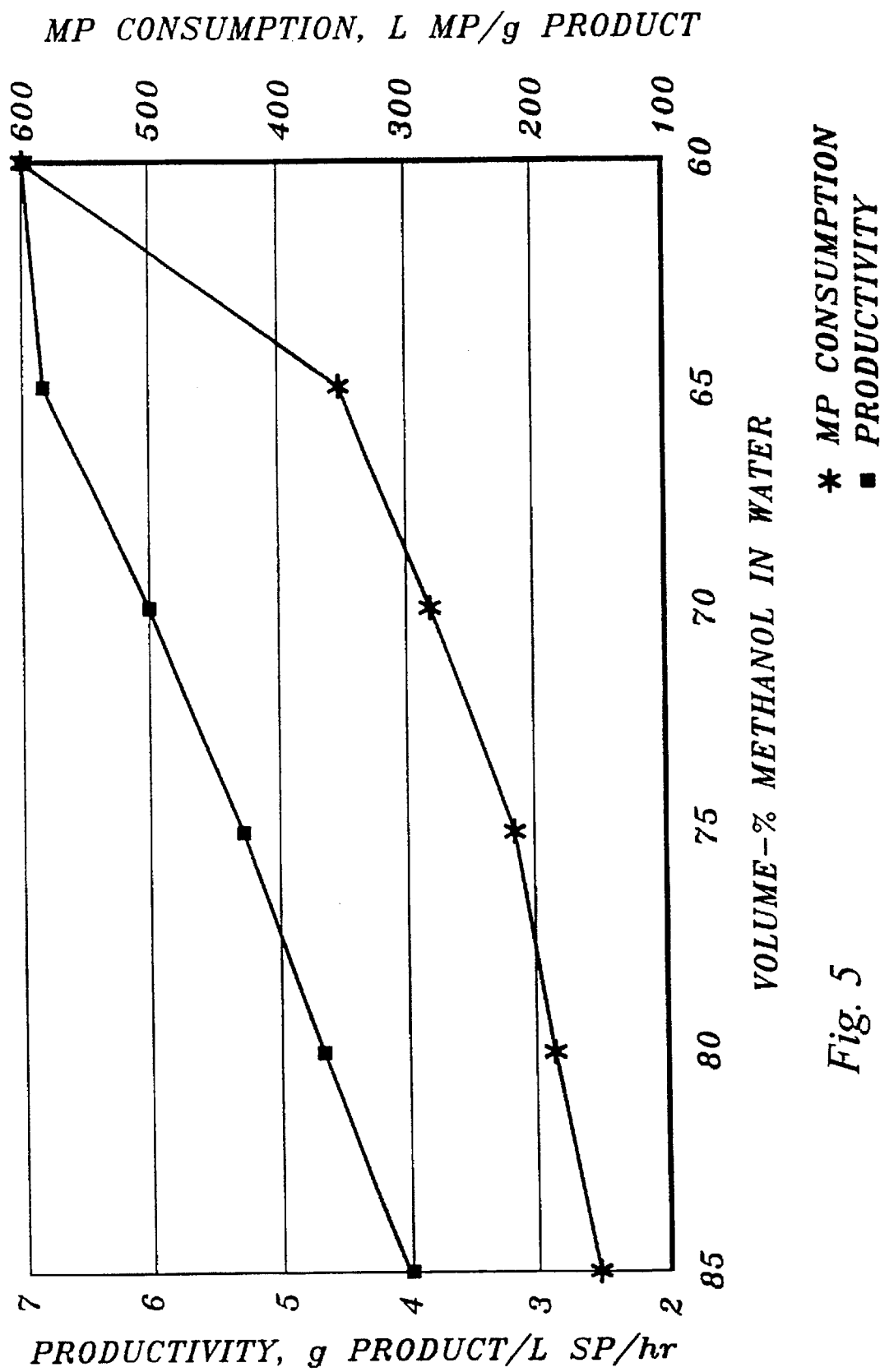
FIG. 5 depicts productivity versus mobile phase consumption.

The optimum separation conditions are with a mobile phase composition of 90/10 vol % methylene chloride/MTBE. At these conditions, the mobile phase consumption is minimized (low capacity factors) and the productivity is relatively high; see FIG. 5.

TABLE 1

| Summary of Elution Profile and SMB Performance Results | | | | | |
|---|---|---|---|---|---|
| MP Comp. Vol-% CH₂Cl₂/MTBE | k' Alpha | k' Beta | ∝ | Prod. | MP Cons. |
| 98/2 | 14.4 | 16.9 | 1.17 | 15.3 | 2,169 |
| 97/3 | 7.1 | 8.1 | 1.14 | 12.1 | 1,379 |
| 95/5 | 2.9 | 3.2 | 1.12 | 10.0 | 702 |
| 90/10 | 0.82 | 1.0 | 1.25 | 14.6 | 172 |

Productivity is defined as grams product/L stationary phase/hour.
MP Consumption is defined as L mobile phase/kilogram product.

GENERAL GUIDELINES

The solubility of the feed material in the mobile phase is an important criterion for achieving a cost-effective separation using SMB technology. Productivity will be low if the feed has low solubility in the mobile phase of choice and the selectivity of the separation is low. Low productivity leads to high stationary phase requirements.

With high stationary phase costs, the savings in solvent recovery costs are less significant. A cost-effective SMB separation requires that the selectivity of the separation and the life of the stationary phase be maximized. With low stationary phase costs, the solvent recovery costs become significant. In most cases, it is desirable to operate with a mobile phase composition that gives capacity factors less than 1.

From the foregoing, distinctions between SMB and traditional elution chromatography, whether analytical or preparative batch chromatography, are apparent. In preparative chromatography, high resolution is required to obtain high purity and recovery. Resolution is proportional to k' and the use of low k''s can result in low resolution. With SMB operation, however, good resolution (greater than 1) is not required. The countercurrent mode of operation is inherently more efficient and high purity and recovery can be achieved by "peak shaving." From the perspective of the elution chromatographer, the use of low values of k' in SMB operation is unexpected. Successful separations via SMB using weakly interacting adsorbents as the stationary phase can be routinely achieved working at a resolution less than 1, contrary to the current guidelines for elution chromatography. See, e.g., Kirkland and Snyder, page 52, who teach that the optimum k' range in elution chromatography is between 1 and 10.

Specifically, for cases where $k'<1$ the chromatographic resolution, Rs, is necessarily less than 0.5. But at these conditions for separation of a 1:1 mixture of 2 components the cutoff at the midpoint of the eluted peak affords 84% purity with about 84% recovery; see p. 34, FIG. 2.11 and page 48, FIG. 2.21, of Kirkland and Snyder, op. cit. However, working with SMB at an Rs of 0.5 one can readily obtain a purity of 95% at a recovery of 95%, which dramatically demonstrates the unexpected difference between elution chromatography and the SMB process. Separating materials with a purity of at least 98% and a recovery of at least 98% is a more preferred mode of operation and is generally readily achievable according to the practice of our invention.

What is claimed is:

1. In a process for the separation of at least one material from a mixture of organic materials by simulated moving bed chromatography using a weakly interacting adsorbent as a solid stationary phase, said adsorbent selected from the group consisting of silica, alumina, titania, magnesia, and layered double hydroxides, the improvement comprising effecting said separation using a liquid mobile phase which affords a retention capacity, k', such that $0.1<k'<1.0$.

2. The process of claim 1 where the separation affords at least one of the organic materials in at least 95% purity with at least 95% recovery.

3. The process of claim 1 where the separation affords at least one of the organic materials in at least 98% purity with at least 98% recovery.

* * * * *